(12) United States Patent
Ghosh et al.

(10) Patent No.: US 12,417,858 B2
(45) Date of Patent: Sep. 16, 2025

(54) DEVICE TO FACILITATE SAFE TRANSPORT OF MEDICAL RADIOISOTOPE SYSTEMS

(71) Applicant: Jubilant Draximage Inc., Kirkland (CA)

(72) Inventors: Tanima Ghosh, Kirkland (CA); Chadi Baida, Kirkland (CA); Michael Gertsenchtein, Kirkland (CA); Steve Mupenda, Kirkland (CA); Indranil Nandi, Yardley, PA (US)

(73) Assignee: Jubilant Draximage Inc. (CA)

( * ) Notice: Subject to any disclaimer, the term of this patent is extended or adjusted under 35 U.S.C. 154(b) by 371 days.

(21) Appl. No.: 18/182,430

(22) Filed: Jun. 12, 2023

(65) Prior Publication Data

US 2024/0047090 A1 Feb. 8, 2024

(51) Int. Cl.
| | |
|---|---|
| *G21F 5/14* | (2006.01) |
| *G16H 40/40* | (2018.01) |
| *G16H 40/67* | (2018.01) |
| *G21F 5/00* | (2006.01) |
| *G21F 5/015* | (2006.01) |
| *G21G 1/00* | (2006.01) |

(52) U.S. Cl.
CPC .............. *G21F 5/14* (2013.01); *G16H 40/40* (2018.01); *G16H 40/67* (2018.01); *G21F 5/015* (2013.01); *G21G 1/0005* (2013.01)

(58) Field of Classification Search
CPC ........... G21F 5/14; G21F 5/015; G16H 40/67; G16H 40/40; G21G 1/0005
See application file for complete search history.

(56) References Cited

U.S. PATENT DOCUMENTS

2019/0247050 A1 * 8/2019 Goldsmith ................ A61F 2/82

OTHER PUBLICATIONS

DE 2942384 C2 (Year: 1990).*

\* cited by examiner

*Primary Examiner* — Nicole M Ippolito
(74) *Attorney, Agent, or Firm* — William D. Hare; McNeely, Hare & War, LLP

(57) ABSTRACT

The present invention relates to a medical radioisotope transport system that securely holds the radiopharmaceutical imaging system or medical elution system to the floor of a vehicle and ensures the protection of the elution system during transportation. The transport system as per the present invention includes at least a floor-mounting device, a support mechanism with transportation plates, and a locking device. The transport system as per the present invention is encompassed with advanced technical and safety features to ensure safe transportation of radiopharmaceuticals ensuring compliance to the regulatory and quality requirements. The transport system as per the present invention is easy to use, and successfully overcome all the complexities involved in prior available methods for transportation of radiopharmaceutical imaging systems or medical radioisotope elution systems.

20 Claims, 6 Drawing Sheets

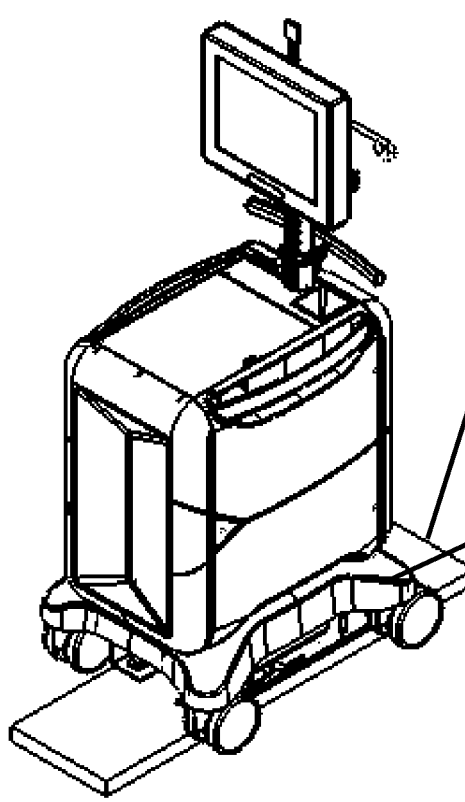
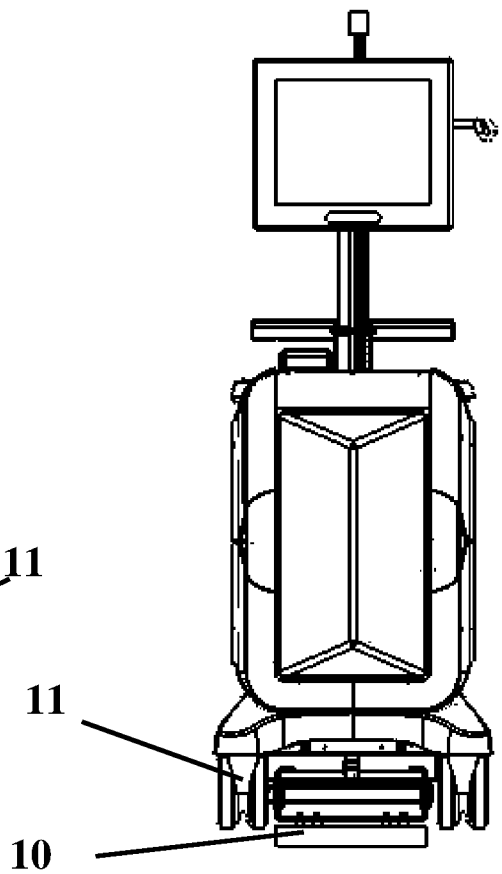
Figure 5A
Figure 5B

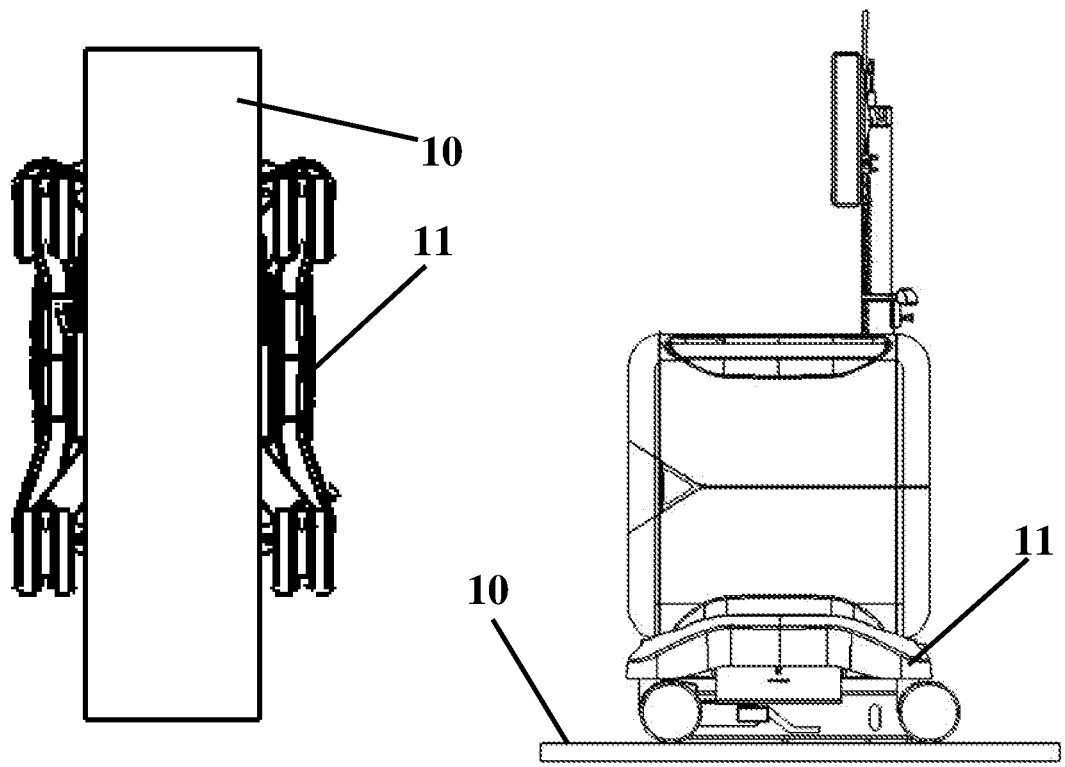
Figure 5E
Figure 5F
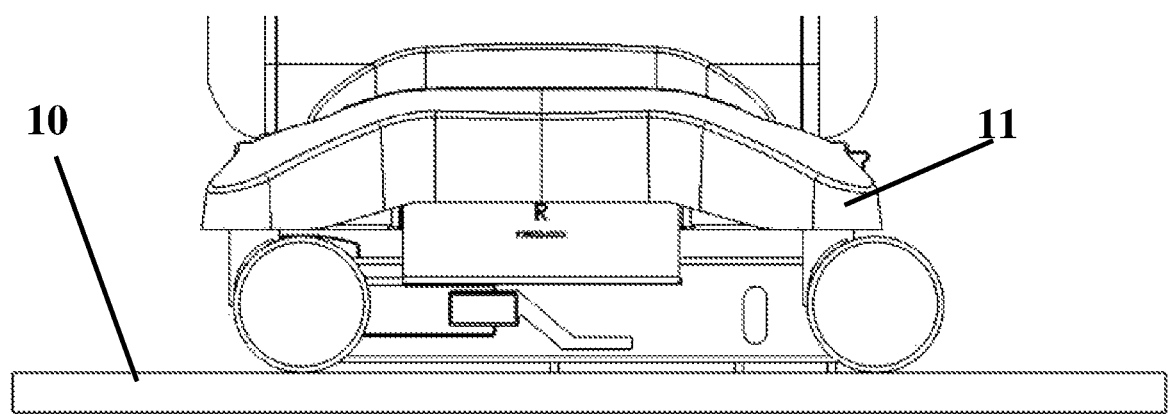
Figure 5G

DEVICE TO FACILITATE SAFE TRANSPORT OF MEDICAL RADIOISOTOPE SYSTEMS

TECHNICAL FIELD OF THE INVENTION

The present invention relates in general to a medical radioisotope transportation device and mechanism with enhanced safety features and a process implementing the same.

BACKGROUND OF THE INVENTION

Radioisotopes play a pivotal role in the diagnosis and mitigation of various disease conditions. For example, $^{60}$Co in treatment of cancer, $^{131}$I in treatment of hyperthyroidism, $^{14}$C in breath tests, $^{99m}$Tc, and $^{82}$Rb as tracers in myocardial perfusion imaging. Rubidium ($^{82}$Rb) is one such compound used as a positron emission tomography (PET) tracer for the non-invasive measurement of myocardial perfusion. The half-lives of some radiopharmaceuticals are very short. Thus, the whole imaging and administration procedure effectively needs to be completed within a very short time period. Due to these challenges, radiopharmaceuticals are usually prepared at on-site facilities having a suitable driving distance from the patient site to prevent undue decay of the radiopharmaceutical prior to use. Moreover, radiopharmaceutical systems carry radiation hazards hence safe transportation is essentially required to avoid any safety hazards.

Regulatory authorities such as USFDA (United States Food and Drug Administration) have set stringent rules and regulations for the safe transportation of radiopharmaceuticals due to harmful effects involved with undesirable and hazardous exposure to radioactive materials. However, due to the complexities involved and stringent regulatory requirements, the presently available tools are not cost-effective and complex in nature.

Hence, there exists an unmet urgent need for an advanced, simple, and cost-effective medical radioisotope transportation device and mechanism with enhanced safety features and without requiring a large capital investment. The transport system as per the present invention fulfills all parameters established by regulatory authorities such as USFDA. The transport system as per the present invention fulfills an unmet need by providing easy and safe access of imaging facilities to patients, hospitals, and radio pharmacies without large capital investment. The transport system as per the present invention securely holds the medical radioisotope elution system to the floor of a vehicle and ensures protection from any undesirable damage to the medical radioisotope elution system during transportation without changing any quality parameters of the elution system. The transport system as per the present invention can be used to securely lock the elution system in a vehicle such as a truck, van or trailer and can also be used to load or unload the elution system from the vehicle based on the need of the user or patient site.

SUMMARY OF THE INVENTION

The present invention aims to provide a medical radioisotope transportation device and mechanism with enhanced safety features and a process for implementing such system.

It is an object of the present disclosure to enhance the safety of the radiopharmaceutical systems during transportation.

It is an object of the present invention to provide a medical radioisotope transport system.

It is an object of the present disclosure to provide a medical radioisotope transport system that securely holds the mobile medical radioisotope elution system to the floor of a vehicle and ensures the protection of the elution system during transportation and use.

It is also an object of the present disclosure to provide a process for implementing the medical radioisotope transport system as per the present invention to the floor of a vehicle to ensure the protection of the mobile medical radioisotope elution system during transportation and use.

BRIEF SUMMARY OF DRAWINGS

Further features and advantages of the present invention will become apparent from the following detailed description, taken in combination with the appended drawings, in which.

DETAILED DESCRIPTION

Figure 1:
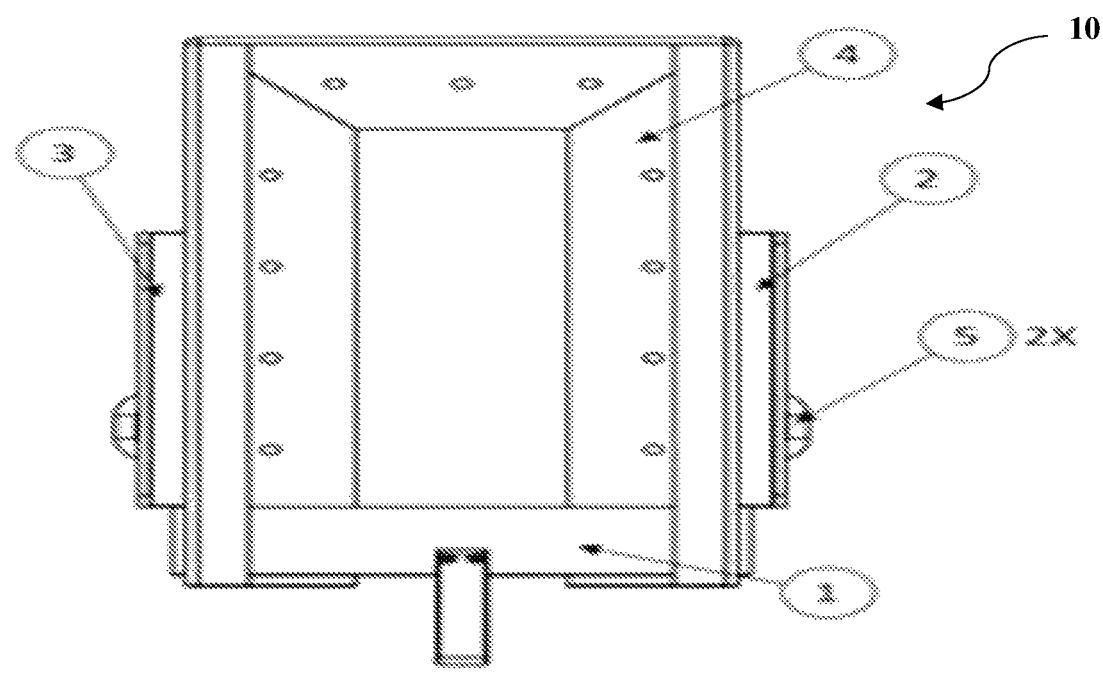
FIG. 1 shows a diagram of a schematically top view of a floor mounting system demonstrating principal elements in accordance with an embodiment of the present invention.
Figure 2:
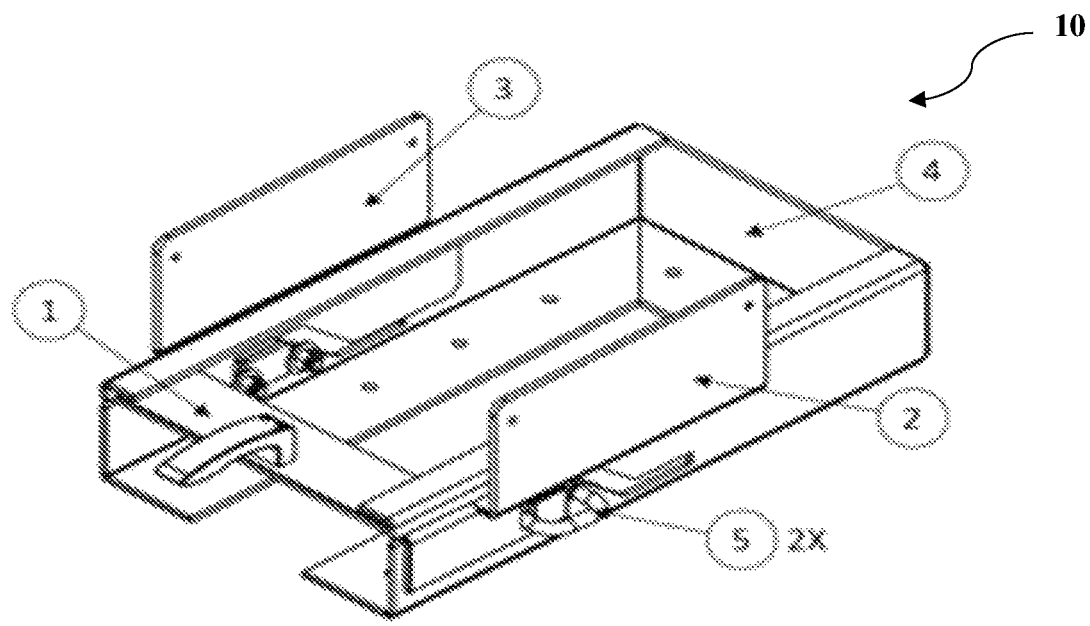
FIG. 2 shows a diagram of a schematically top diagonal view of the floor mounting system of FIG. 1 demonstrating principal elements in accordance with an embodiment of the present invention.
Figure 3:
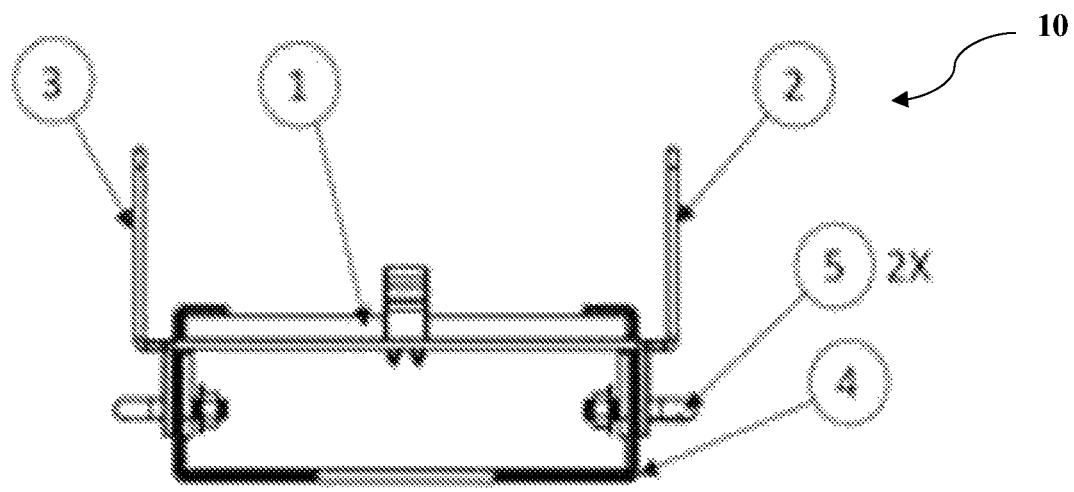
FIG. 3 shows a diagram of a schematically front view of the floor mounting system of FIG. 1 demonstrating principal elements in accordance with an embodiment of the present invention.

Exemplary embodiments are described in the following description with reference to the drawings. The drawings are not necessarily true to scale but are rather intended to schematically illustrate examples of the particular features. It should be noted that the features and components described in the following can be combined with each other independently of whether they were described in conjunction with a single embodiment. The combination of features in the respective embodiments serves only to illustrate the basic construction and the function of the claimed device.

FIGS. 1-4 illustrate diagrams of floor mounting system (10), demonstrating principal elements in accordance with an embodiment of the present invention. The floor mounting system (10) includes a locking frame with a handle (1) that helps to move the elution system in a floor-mounted position. The floor mounting system (10) also includes a system plate left (2) and a system plate right (3) that help to hold and/or securely fix the elution system on the floor mounting system (10). A floor frame or docking station (4) holds the whole floor mounting system (10) to the floor of a vehicle/truck/van/trailer, etc. and a metal bar with a padlock (5) secures the elution system to the floor frame or docking station.

Figure 4:
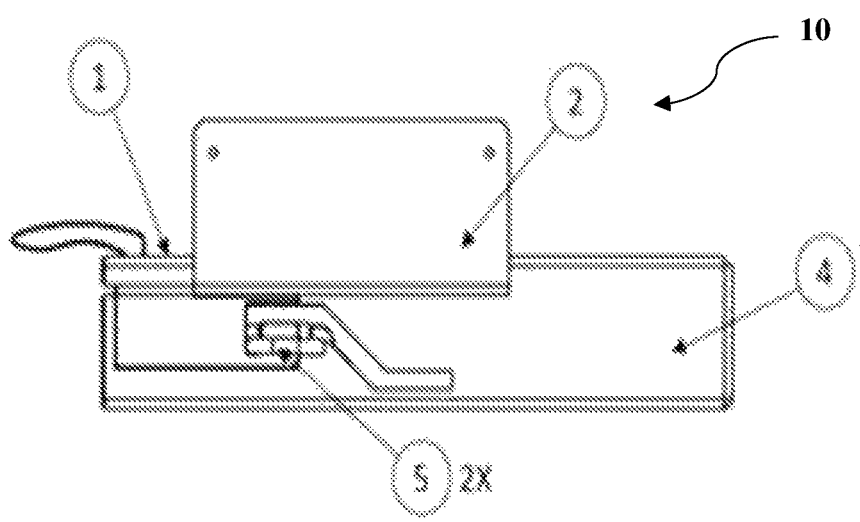
FIG. 4 shows a diagram of a schematically side view of the floor mounting system in accordance with another embodiment of the present invention.

FIG. 4 illustrates diagrams of the side view of the floor mounting system (10) and diagonal view of a locking plate subassembly respectively which depict the mechanism of a metal bar with a padlock (5) to secure the elution system to the floor frame or docking station (4) effectively.

Figure 5:
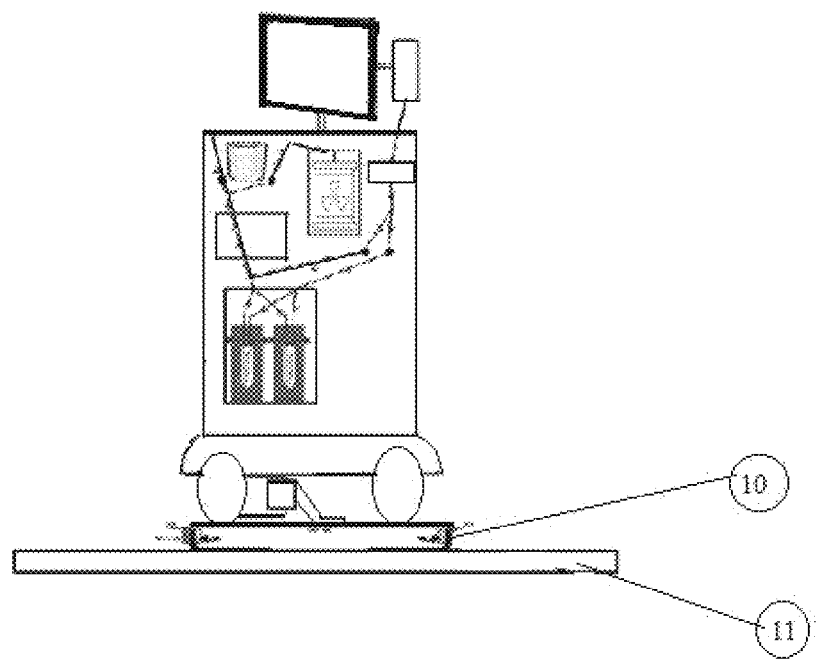
FIG. 5 shows a diagram of an elution system located over a floor mounting system in accordance with another embodiment of the present invention.
Figure 5C:
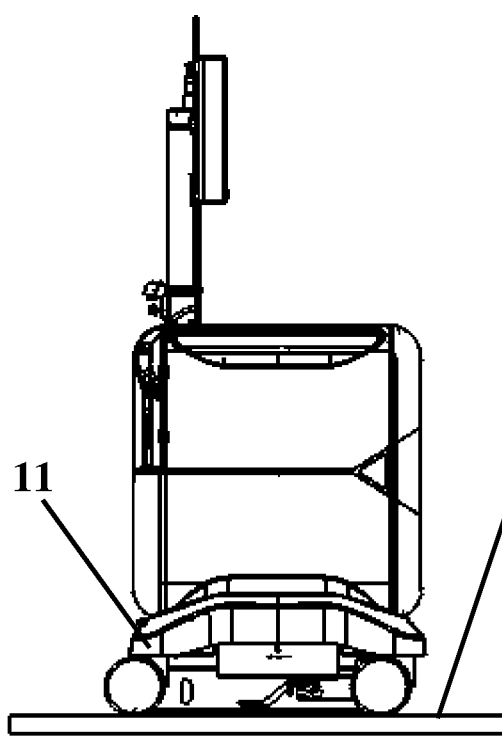
Figure 5D:
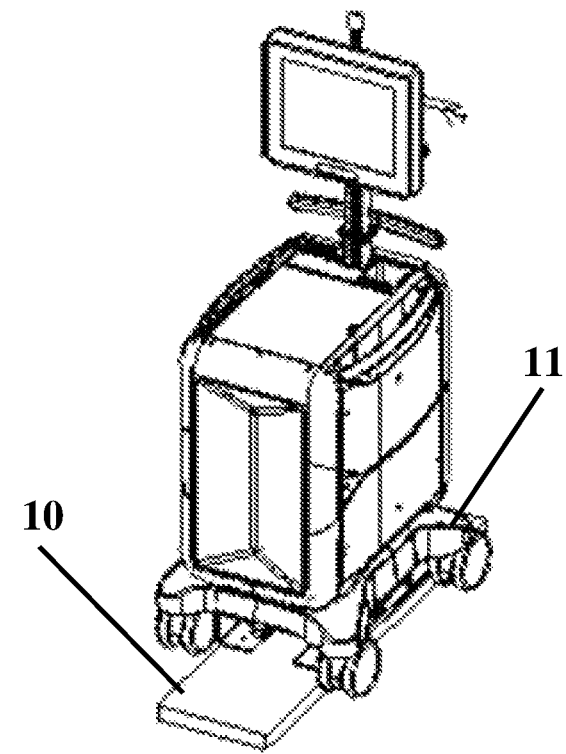

FIG. 5 illustrates a side view of an elution system located over a floor mounting system (10) which is placed on a vehicle floor (11). The elution system slides over the mounting system, which is located or fixed on the floor of the vehicle and an engaging attachment is installed on the base of the elution system to get it locked with the mounting system via the lock handle.

The present disclosure provides a medical radioisotope transport system that securely holds the mobile medical radioisotope elution system inside a vehicle and ensures protection of the elution system during transportation and use.

The present disclosure provides a medical radioisotope transport system that securely holds the mobile medical radioisotope elution system to the floor of a vehicle and ensures protection of the elution system during transportation and use.

The medical radioisotope transport system or equipment as per the present invention is interchangeable with the term "mobile adaptation kit" or "mobile adaptation setup" or "mobile adaptation kit setup" or "mobile adaptation kit assembly". The terms used herein such as trailers, van, truck, vehicle, are interchangeable and should be meant in a way to encompass any vehicle which is used or suitable for the transportation/delivery/movement/loading/unloading of medical elution system.

As used herein, the "mobile medical radioisotope elution system" according to the present invention comprises one or more systems for dispensing a radioactive dose.

In an embodiment according to the present invention, there is provided a system comprising an integrated locking mechanism including combined bar, bolt, padlock and strap.

In an embodiment according to the present invention, there is provided a medical radioisotope transport system comprising:
  a floor-mounted device in transport vehicle configured to support mobile medical radioisotope elution system;
  a support mechanism with transportation plates configured to support the mobile medical radioisotope elution system; and
  a locking device configured to securely and tightly connect the floor-mounted device and the support mechanism with transportation plates.

In an embodiment according to the present invention, there is provided a medical radioisotope transport system comprising:
  a floor-mounted device in transport vehicle configured to support mobile medical radioisotope elution system;
  a support mechanism with transportation plates configured to support the mobile medical radioisotope elution system; and
  a locking device configured to securely and tightly connect the floor-mounted device and the support mechanism with transportation plates;
  wherein the said transport system securely holds the medical radioisotope elution system to the floor of a vehicle and ensures protection from any undesirable damage to the medical radioisotope elution system during transportation.

In an embodiment according to the present invention, there is provided a medical radioisotope transport system comprising:
  a floor-mounted device in transport vehicle configured to support mobile medical radioisotope elution system;
  a support mechanism with transportation plates configured to support the mobile medical radioisotope elution system;
  a locking device configured to securely and tightly connect the floor-mounted device and support mechanism with transportation plates;
  the floor-mounting device is configured to further consist of a handle, at least two system plates, a floor frame, and at least a metal bar with a padlock to secure the equipment to the docking station; and
  the mobile medical radioisotope elution system is configured to store at least one or more doses of nuclear medicine;
  wherein the said transport system securely holds the mobile medical radioisotope elution system to the floor of a vehicle and ensures protection of the mobile medical radioisotope elution system with a radioisotope generator during transportation and
  wherein the said transport system is free of any tie-down straps or rings to hold the mobile medical radioisotope elution system within a vehicle.

In an embodiment according to the present invention, there is provided a strontium-rubidium radioisotope elution transport system comprising:
  a floor-mounted device in a transport vehicle configured to support radioisotope elution system;
  a support mechanism with transportation plates configured to support the radioisotope elution system;
  a locking device configured to securely and tightly connects floor-mounted device and support mechanism with transportation plates; and
  the floor-mounting device is configured to further consist of a handle, at least two system plates, a floor frame, and at least a metal bar with a padlock to secure the equipment to the docking station; and
  the radioisotope elution system is configured to store at least one or more doses of nuclear medicine;
wherein the said transport system securely holds the strontium-rubidium elution system to the floor of a vehicle and ensures protection of the elution system with a radioisotope generator during transportation and wherein the said transport system is free of any tie-down straps or rings to hold the radioisotope elution system within a vehicle.

In an embodiment according to the present invention, the floor-mounting device comprises at least one or more locking frames with a handle, system plate, floor frame, and one or more bolts.

In an embodiment according to the present invention, the floor-mounting device comprises at least one or more locking frames with a handle, system plate, floor frame, and a metal bar with a padlock to secure the equipment to the docking station.

In an embodiment according to the present invention, the mobile medical radioisotope elution system comprises Rb-82 (Rubidium-82), O-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), and Zr-89 (Zirconium-89). In an embodiment according to the present invention, the mobile medical radioisotope elution system comprises Lutetium Lu-177, Rhenium-188, Ac-224, Zr-89, and Ra-223 isotope compounds. In a preferred embodiment according to the present invention, the mobile medical radioisotope elution system comprises a strontium-rubidium elution system.

In an embodiment according to the present invention, the radiopharmaceutical elution has source of radiopharmaceutical selected from Technetium-99m($^{99m}$Tc), Iodine-123 ($^{123}$I), Iodine 124 ($^{124}$I), Iodine-125($^{125}$I), Iodine-131($^{131}$I), Sodium Iodide ($^{123}$I, $^{124}$I, $^{125}$I, $^{131}$I), Phosphorous-32($^{32}$P), Indium-111($^{111}$In), Cobalt-57($^{57}$Co), Erbium-169($^{169}$Er), Gallium-67 ($^{67}$Ga), Gallium-68 ($^{68}$Ga), Ammonia-13($^{13}$N), Sodium fluoride($^{18}$F), Flourine-18 ($^{18}$F), Lutetium Lu-177 ($^{177}$Lu), Radium-223 ($^{223}$Ra), Samarium-153 ($^{153}$Sm), Thallium-201 ($^{201}$Tl), Yttrium-90($^{90}$Y), Chromium-51 ($^{51}$Cr), Holmium-166($^{166}$Ho), Rhenium-186($^{186}$Re), Rhenium-188 ($^{188}$Re), Rubidium-81 ($^{81}$Rb), Strontium-89 ($^{89}$Sr), Actinium-225 ($^{225}$Ac), Xenon-133 (Xe-133), and Gold-198 ($^{198}$Au).

In an embodiment according to the present invention, the radiopharmaceutical dispensing system may include various components like a controller, pumps, valves, sensors, radiopharmaceutical source, cabinet, shielded assembly, shielded chambers, tubing, activity detector, dose calibrator, computer, internal memory, user interface, motors, syringes, pipettes, needles, exhaust, filters, and other accessories. Radiopharmaceutical dispensing systems may be connected to one or more equipment or networks like imaging systems, infusion systems, hospital networks, pharmacies, servers, remote computers, iPads, mobile tablets, mobile phones, watches, or like. The radiopharmaceutical dispensing system may be connected via wired or wireless connections like Local Area Network (LAN), internet, communication ports, Wireless Fidelity (Wi-Fi), Universal Serial Bus (USB), Bluetooth, Cables, Compact Disc, Digital Video Disc and/or combinations thereof.

In an embodiment according to the present invention, the system permits one to transport mobile medical radioisotope elution system with a radioisotope generator in a vehicle such as a truck or a van, or a trailer.

In an embodiment according to the present invention, the transport system is free of any tie-down straps used to hold the mobile medical radioisotope elution system within a vehicle.

In an embodiment according to the present invention, the transport system is free of any mechanism, assembly or setup wherein the mobile medical radioisotope elution system is fixed using straps to a bracket located on the floor of the vehicle.

In an embodiment according to the present invention, the transport system is free of any mechanism, assembly or setup wherein the mobile medical radioisotope elution system is fixed using straps, elastic, rope, belt, hook, buckle or ratchet to a bracket located on the floor of the vehicle.

In an embodiment according to the present invention, the transport system is free of any tie-down rings used to hold the mobile medical radioisotope elution system with a radioisotope generator within a vehicle.

In an embodiment according to the present invention, the transport system is free of any tie-down wires used to hold the mobile medical radioisotope elution system with a radioisotope generator within a vehicle.

In an embodiment according to the present invention, the transport system is used to permanently lock the mobile medical radioisotope elution system in a vehicle such as a truck, van, or trailer.

In an embodiment according to the present invention, the transport system enables the mobile medical radioisotope elution system for use in both fixed trailers, van or truck and mobile on-site delivery as per hospital or patient's need.

In an embodiment according to the present invention, the transport system is used to load or unload the mobile medical radioisotope elution system from a vehicle such as a truck, van, or trailer based on the need of the user.

In an embodiment according to the present invention, the transport system is used to load the mobile medical radioisotope elution system by fixing it on a frame and securing it with a locking-unlocking device.

In an embodiment according to the present invention, the transport system comprises a plurality of wheels configured with brake mechanisms. In another embodiment according to the present invention, the transport system comprises a plurality of wheels configured without brake mechanisms.

In an embodiment according to the present invention, the transport system comprises a shock-absorbing mechanism.

In an embodiment according to the present invention, the mobile medical radioisotope elution system further comprises a locking device to secure the radioisotope inside the elution system.

In an embodiment according to the present invention, the mobile medical radioisotope elution system further comprises a locking device for the generator lead well.

In an embodiment according to the present invention, the mobile medical radioisotope elution system comprises a device for securing the dose calibrator during transportation.

In an embodiment according to the present invention, the mobile medical radioisotope elution system comprises an arrangement for securing the computer, all hardware, and all software of the elution system during transportation.

In an embodiment according to the present invention, the transport system further comprises a sensor system.

In an embodiment according to the present invention, the sensor system further comprises at least one or more sensors such as a temperature sensor, pressure sensor, motion sensor, vibration sensor, current sensor, speed sensor, and voltage sensor.

In an embodiment according to the present invention, the transport system further comprises an alarm system. In another embodiment, the alarm system shall provide audible and/or visual alerts/alarms to the operator or user. In case any problem or undesirable activity in the elution system occurs such as any leakage, damage, missing of any part, any default in any part of the device, the system will provide the alert and/or alarm to the operator. In an embodiment, the alarm system shall provide continuously audible and/or visual alerts/alarms to the operator or user in case the elution system is not properly or loosely connected with the transport system.

In an embodiment according to the present invention, the mobile medical radioisotope transport or elution system comprises a navigation and/or tracking systems such as GPS (global positioning system) device which provide accurate position, velocity, and time information of vehicles or elution system. In another embodiment, the tracking system simultaneously can provide real-time data such as accurate position, velocity, and time information of vehicles or elution system to multiple locations such as loading location, delivery location, radiopharmacy, or hospital location. In an embodiment, the navigation and/or tracking system of mobile medical radioisotope elution system can be connected to the GPS system of a truck or van, or trailer. In an embodiment, the navigation and/or tracking system of the mobile medical radioisotope elution system can provide audible and/or visual alerts/alarms to the operator or user, in case there is any change and/or error in route direction. In an embodiment, the navigation and/or tracking system enable the users to share audible and/or visual alerts/alarms or messages to each connected user located at various locations. In an embodiment, the system is equipped with one or more of microprocessor modules, LCD touch control display module, Access Port module, GPRS wireless communication module, GPS global positioning module, data memory module, Bluetooth module, LCD touch control display module, and/or wireless sensor network module electrically connected.

In an embodiment according to the present invention, the mobile medical radioisotope transport or elution system comprises a damage avoidance system that is activated once the risk of damage is detected, before impact with the surface or air. To illustrate a specific example, the mobile medical radioisotope elution system is equipped with a damage avoidance system that includes a safety monitoring system and/or a protection system. In this sense, a damage avoidance system comprises one or more protection elements working together to reduce or prevent damage to the elution system on hitting the surface or any hard object. In an embodiment, the protection system deploys an airbag before the elution system hits any hard object or surface. The airbag will absorb the impact and protect the system to reduce or eliminate damage.

In an embodiment according to the present invention, the medical radioisotope transport system maintains the system functionality as per the manufacturer's specification throughout the loading-unloading and transportation process.

In an embodiment according to the present invention, the medical radioisotope transport system secures the generator, computer, waste bottle, and other critical components throughout the loading-unloading and transportation process.

In an embodiment according to the present invention, the transport system further comprises a locking-unlocking system. In another embodiment, the locking-unlocking system is a lock and key-based system. In another embodiment, the locking-unlocking system is a numbering-based system. In another embodiment, the locking-unlocking system is a biometric-based system. In another embodiment, the biometric locking-unlocking system is operated through fingerprints, thumbprints, retina of operator or user, or like.

In an embodiment according to the present invention, the transport system further comprises a power backup system configured to provide power with at least one power storage device.

In an embodiment according to the present invention, the transport system further comprises a monitoring device navigation system to estimate the location of the system.

In an embodiment according to the present invention, the transport system further comprises a monitoring device configured to connect to a wireless network and exchange information across the wireless network to the mobile medical radioisotope elution system.

In an embodiment according to the present invention, the system plates comprise at least two plates located on the left and right sides of the floor-mounting device.

In an embodiment according to the present invention, the one or more bolts used in the floor-mounting device are U-bolts. In another embodiment, the system comprises a metal bar with a padlock to secure the equipment to the docking station.

In an embodiment according to the present invention, there is provided a strontium-rubidium radioisotope elution transport system comprising one or more adaptation kits, a frame locking system, generator door locking system, generator padding, computer stabilization, dose calibrator locking, and waste bottle.

In an embodiment according to the present invention, there is provided a strontium-rubidium elution system comprising an attachment for engaging the elution system over the mounting system, wherein the mounting system is attached or fixed to the base of the vehicle.

In an embodiment according to the present invention, there is provided a method to transport a strontium-rubidium elution system with enhanced safety features, wherein the method comprises complete quality control testing of the elution system after completion of transport with one or more tests, including but not limited to, visual inspection, and installation qualification test.

In another embodiment, the technical integrity of the elution system is tested using one or more following methods: a) verifying all tubings remain properly installed with the strontium-rubidium elution system; b) verifying pressure transducer remains plugged into the strontium-rubidium elution system; c) verifying that all valves e.g. pinch valves are intact or not damaged; d) verifying that tubing within the activity counter is properly installed and the door is properly closed; e) verifying that pump is intact or not damaged, and f) verifying that UPS is powered on.

What is claimed:

1. A medical radioisotope transport system comprising:
a floor-mounted device in a transport vehicle configured to support mobile medical radioisotope elution system;
a support mechanism with transportation plates configured to support the mobile medical radioisotope elution system; and
a locking device configured to securely and tightly connect the floor-mounted device and the support mechanism with transportation plates;
wherein the said transport system securely holds the medical radioisotope elution system to the floor of a vehicle and ensures protection from any undesirable damage to the medical radioisotope elution system during transportation.

2. The medical radioisotope transport system according to claim 1, wherein the floor-mounting device comprises at least one or more locking frames with a handle, system plate, floor frame, and a metal bar with a padlock.

3. The medical radioisotope transport system according to claim 1, wherein the mobile medical radioisotope elution system comprises a strontium-rubidium elution system.

4. The medical radioisotope transport system according to claim 1, wherein the system permits to transport the mobile medical radioisotope elution system with a radioisotope generator in a vehicle such as a truck or a van, or a trailer.

5. The medical radioisotope transport system according to claim 1, wherein the transport system is free of any tie-down straps or rings used to hold the mobile medical radioisotope elution system within a vehicle.

6. The medical radioisotope transport system according to claim 1, wherein the transport system is used to permanently lock the mobile medical radioisotope elution system in a vehicle such as a truck or a van, or a trailer.

7. The medical radioisotope transport system according to claim 1, wherein the transport system is used to load or unload the mobile medical radioisotope elution system from a vehicle such as a truck or a van, or a trailer based on the need of the user.

8. The medical radioisotope transport system according to claim 1, wherein the transport system comprises a plurality of wheels configured with brake mechanisms.

9. The medical radioisotope transport system according to claim 1, wherein the transport system comprises a shock-absorbing mechanism.

10. The medical radioisotope transport system according to claim 1, wherein the mobile medical radioisotope elution system further comprises a locking device for the generator lead well.

11. The medical radioisotope transport system according to claim 1, wherein the mobile medical radioisotope elution system further comprises a device for securing the dose calibrator chamber during transportation and use.

12. The medical radioisotope transport system according to claim 1, wherein the mobile medical radioisotope elution system further comprises an arrangement for securing the computer during transportation and use.

13. The medical radioisotope transport system according to claim 1, wherein the transport system further comprises a sensor system.

14. The sensor system according to claim 13, wherein the sensor system further comprises at least one or more sensors such as a temperature sensor, pressure sensor, motion sensor, current sensor, and voltage sensor.

15. The medical radioisotope transport system according to claim 1, wherein the transport system further comprises a power backup system configured to provide power with at least one power storage device.

16. The medical radioisotope transport system according to claim 1, wherein the transport system further comprises a monitoring device navigation system to estimate the location of the system.

17. The medical radioisotope transport system according to claim 1, wherein the transport system further comprises a monitoring device configured to connect to a wireless network and exchange information across the wireless network to the mobile medical radioisotope elution system.

18. The floor-mounting device according to claim 2, wherein the system plates comprises at least two plates located on the left and right side of the floor-mounting device.

19. The floor-mounting device according to claim 2, wherein the metal bar with a padlock is used to secure the equipment to the docking station.

20. A strontium-rubidium radioisotope elution transport system comprising:
   a floor-mounted device in transport vehicle configured to support radioisotope elution system;
   a support mechanism with transportation plates configured to support the radioisotope elution system;
   a locking device configured to securely and tightly connects floor-mounted device and support mechanism with transportation plates; and
   the floor-mounting device is configured to further consist of a handle, at least two system plates, a floor frame, and at least a metal bar with a padlock to secure the equipment to the docking station; and
   the radioisotope elution system is configured to store at least one or more doses of nuclear medicine;
wherein the said transport system securely holds the strontium-rubidium elution system to the floor of a vehicle and ensures protection of the elution system with a radioisotope generator during transportation and wherein the said transport system is free of any tie-down straps or rings to hold the radioisotope elution system within a vehicle.

* * * * *